(12) United States Patent
Shinozaki

(10) Patent No.: US 6,860,169 B2
(45) Date of Patent: Mar. 1, 2005

(54) MANIPULATION UNIT

(75) Inventor: Junichiro Shinozaki, Chino (JP)

(73) Assignee: Seiko Epson Corporation (JP)

( * ) Notice: Subject to any disclaimer, the term of this patent is extended or adjusted under 35 U.S.C. 154(b) by 73 days.

(21) Appl. No.: 10/261,171

(22) Filed: Sep. 30, 2002

(65) Prior Publication Data

US 2003/0101838 A1 Jun. 5, 2003

(30) Foreign Application Priority Data

Nov. 30, 2001 (JP) .......................................... 2001-367328

(51) Int. Cl.[7] .............................................. B25J 15/00
(52) U.S. Cl. ............................... 74/490.06; 74/490.01; 901/29
(58) Field of Search ........................ 74/490.01, 490.03, 74/490.05, 490.06; 901/23, 24, 25, 29

(56) References Cited

U.S. PATENT DOCUMENTS

| | | | | |
|---|---|---|---|---|
| 864,014 A | * | 8/1907 | Maxwell ...................... | 464/57 |
| 1,826,611 A | * | 10/1931 | Furgason ..................... | 464/11 |
| 4,300,362 A | * | 11/1981 | Lande et al. ................ | 464/117 |
| 4,748,867 A | | 6/1988 | Susnjara | |
| 5,255,571 A | * | 10/1993 | Smith ....................... | 74/490.06 |
| 5,299,465 A | * | 4/1994 | Kasuga ...................... | 74/89.33 |
| 5,738,481 A | * | 4/1998 | Rogers ...................... | 414/744.6 |
| 5,740,699 A | * | 4/1998 | Ballantyne et al. ....... | 74/490.06 |
| 6,619,147 B1 | * | 9/2003 | Kojima ...................... | 74/89.36 |
| 2002/0066331 A1 | * | 6/2002 | Okada et al. ............ | 74/490.03 |

FOREIGN PATENT DOCUMENTS

EP 0 658 405 * 6/1995

* cited by examiner

Primary Examiner—William C. Joyce
(74) Attorney, Agent, or Firm—Harness, Dickey & Pierce, P.L.C.

(57) ABSTRACT

3-degrees-of-freedom universal joints UJ1 and UJ2 for allowing the hand H1 to make up-down swing motions D1 and side-to-side swing motions D2 are joined to the top right and left parts, respectively, of the wrist portion of the hand H1, and a 2-degrees-of-freedom universal joint UJ3 for allowing the hand H1 to make twisting rotations D3 is joined to the wrist portion of the hand H1 so as to serve as the center of 3-degrees-of-freedom.

1 Claim, 8 Drawing Sheets

(a)

(b)

MANIPULATION UNIT

DETAILED DESCRIPTION OF THE INVENTION

1. Field of the Invention

The present invention relates to manipulation units and is particularly suited to application in robot hands, manipulators and the like.

2. Description of the Related Art

Industrial robots have conventionally been equipped with a securing/gripping hand utilizing parallel link mechanisms, such as described for instance in Laid-Open Japanese Patent Application No. 9-285874. Further, there have been humanoid robots having a single-point intersection type wrist mechanism allowing the 3 axes of the wrist joint to intersect at a single point by means of gearwheels, as described in the Robot Handbook (Corona Publications).

However, securing/gripping hands utilizing parallel link mechanisms have suffered from the problem that they could not permit 3-degrees-of-freedom because they were joined to an arm with only one or 2-degrees-of-freedom, and this has rendered precision control of their positioning time-consuming.

Further, the method of using gearwheels to realize the single-point intersection type wrist mechanism has rendered the mechanisms more complicated, which has not only prevented the mechanism from being more lightweight and more compact, but also resulted in the additional problem that operation calculations posed difficulties since the rotational axes are not orthogonal to each other.

Accordingly the object of the present invention is to provide a manipulation unit in which the rotation centers of the 3-degrees-of-freedom can be made to coincide at a single point while keeping the rotational axes orthogonal to each other.

SUMMARY OF THE INVENTION

In order to attain the aforesaid object, the invention according to provides a manipulation unit having first and second universal joints that allow up-down and side-to-side swing motions to be made in response to linear motions, and a third universal joint that serves as the center of 3-degrees-of-freedom and execute twisting rotation. This makes it possible to have the rotation centers of 3-degrees-of-freedom coincided at a single point, with the rotational axes kept orthogonal to each other, thus making it possible to make the manipulation unit more lightweight and more compact and permitting kinematical coordinate calculations, so that agile and precise positioning control can be implemented.

The invention also provides a manipulation unit having a first linear actuator that moves the first universal joint in linear motion, a second linear actuator that moves the second universal joint in linear motion, and a rotation motor that rotates the third universal joint. This enables a linear motion of the first and second universal joints and a rotation of the third universal joint, without increasing the mechanism's complexity, thus making it possible to make the manipulation unit more lightweight and more compact.

The invention further provides a manipulation unit additionally having a first drive control means that drives the first and second linear actuators in the same direction so that it corresponds to an up-down swing motion, and a second drive control means that drives the first and second linear actuators in opposite directions so that it corresponds to a side-to-side swing motion.

Accordingly, simple drive control by itself makes up-down and side-to-side swing motions possible, thus permitting simpler computational processing for operational motion and agile and precise positioning control.

The invention, in addition, provides a manipulation unit, wherein the first linear actuator includes a first moving block which connects to the first universal joint via a first connecting rod and in which a first screw groove is cut, a first screw member which is fitted into the first screw groove, and a first motor which rotates the first screw member; and the second linear actuator includes a second moving block which is connected to the second universal joint and into which a second screw groove is cut, a second screw member which is fitted into the second screw groove, and a second motor which rotates the second screw member.

This makes it possible to make up-down and side-to-side swing motions using rotation motors, thus making it possible to make the manipulator unit more compact and less expensive.

The invention also provides a manipulation unit having a first guide groove formed in the direction of the axis of the first screw member and a first projecting portion which is inserted into the first guide groove and is joined to the first moving block, a second guide groove formed in the direction of the axis of the second screw member and a second projecting portion which is inserted into the second guide groove and is joined to the second moving block.

In this way, the moving blocks are moved by engaging with the screw member and therefore they do not rotate, so that the blocks move in linear motion only, thus permitting fine precision positioning of the first and second universal joints.

The invention further provides a manipulation unit, wherein the projecting portions is in contact with the guide grooves via bearings.

This makes it possible to reduce friction between the projecting portions and the guide grooves even when the former comes into contact with the latter, thus permitting smooth execution of linear motion of the moving blocks.

The invention also provides a manipulation unit, wherein the universal joints have stepped bearing screws screwed into the cruciform member through the bearings. This makes it possible to install the bearings to the cruciform member simply by screwing the stepped bearing screws into the cruciform member through the bearings, and to have the bearings rotate around the bearing stepped screws, thus permitting a simpler mechanism for the universal joints.

The invention further provides a manipulation unit having first and second universal joints that allow up-down and side-to-side swing motions to be made in response to linear motion, a third universal joint that serves as the center of 2-degrees-of-freedom and enables twisting rotations, and a rotation means that rotates the first and second universal joints around fixed axes.

This makes it possible to separate the part by which twisting rotation are executed from the part by which up-down and side-to-side swing movements are executed; thus the need to deploy the mechanism for making twisting rotations in the part by which up-down and side-to-side swing movements are executed is eliminated, thereby making it possible to make the manipulation unit more compact and to achieve more simplified control.

The invention also provides a manipulation unit having first and second universal joints that enable up-down and side-to-side swing movements to be made in response to linear motions, a third universal joint that serves as the center of 2-degrees-of-freedom and enables twisting rotations, a first linear actuator which moves the first universal joint in linear motion, a second linear actuator which moves the second universal joint in linear motion, fastening blocks which hold the first, second and third universal joints and the first and second linear actuators securely, a support block which supports the fixing blocks, bearings which support the support block such that it is able to rotate around a fixed shaft, a rotation motor which is installed in the support block, and gearwheels which transmit the rotational force of the rotation motor to the fixed shaft.

This enables the first and second universal joints to rotate on the circumference around the fixed shaft at an angle relative to it, so that positioning control can be implemented with ease even in cases where the part by which twisting rotations are executed is separated from the part by which up-down and side-to-side swing movements are executed.

The invention further provides a manipulation unit, wherein the fastening blocks are fastened to the support block such that the third universal joint is located on the line of the fixed shaft's axis.

This enables a rotation around the X, Y and Z axes in any desired direction, even in cases where the part by which a twisting rotation is executed is separated from the part by which up-down and side-to-side swing movements are executed.

DESCRIPTION OF THE PREFERRED EMBODIMENTS

Preferred embodiments of the manipulation unit according to the present invention are described below, using a robot hand as an example.

Figure 1:
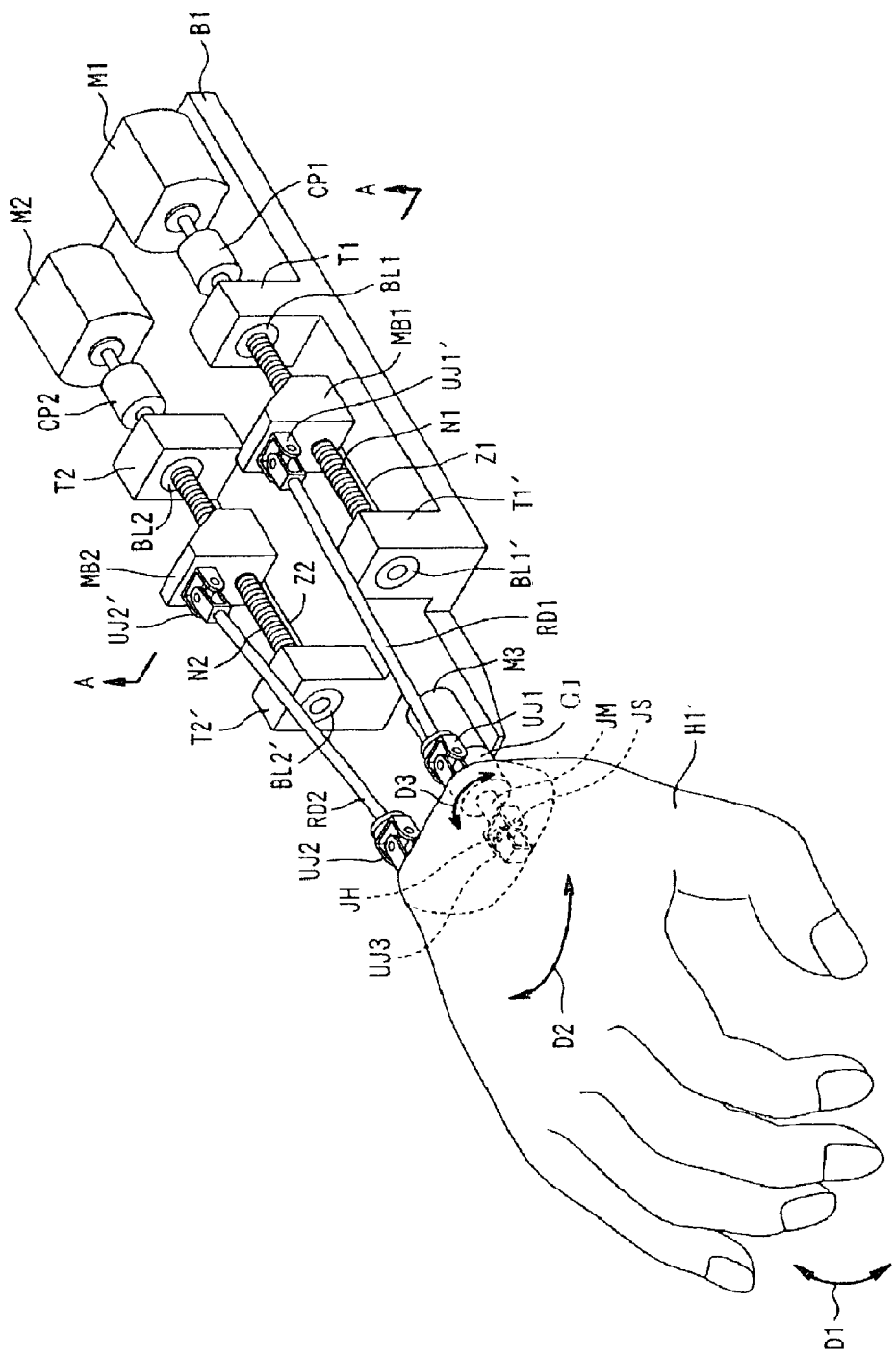
FIG. 1 is a perspective view showing a general configuration of a robot hand according to a first embodiment of the present invention.
Figure 2:
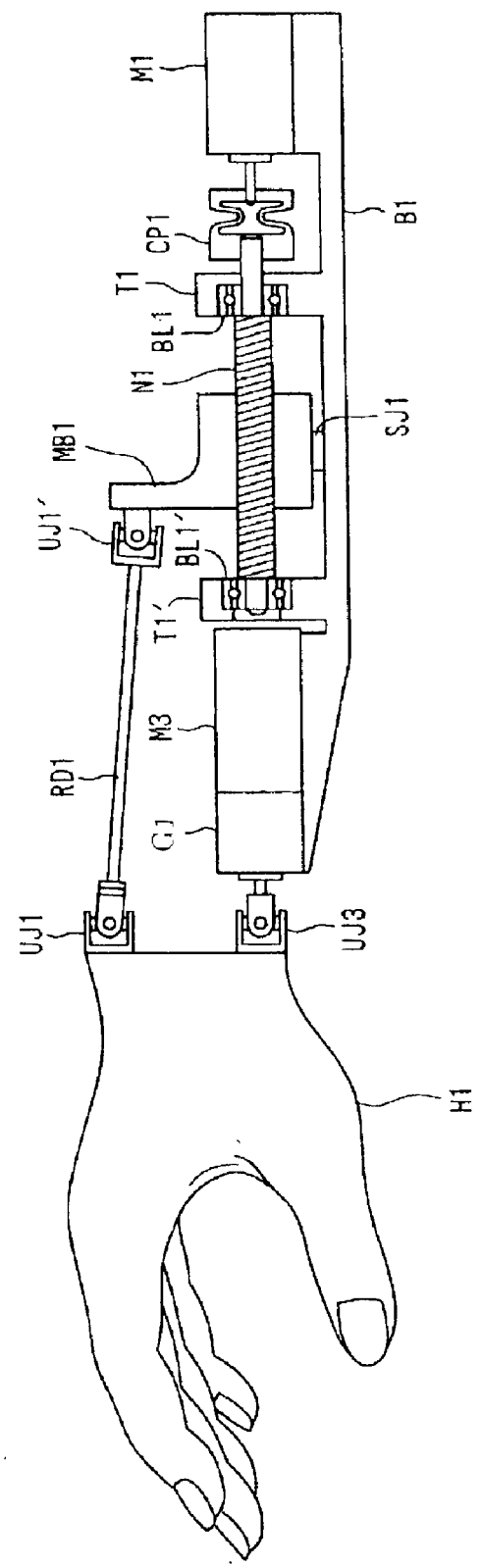
FIG. 2 is a side view showing a general configuration of a robot hand according to the first embodiment of the present invention.

FIG. 1 is a perspective view showing a general configuration of a robot hand according to a first embodiment of the present invention. FIG. 2 is a side view showing a general configuration of the robot hand according to the first embodiment of the present invention.

Figure 3:
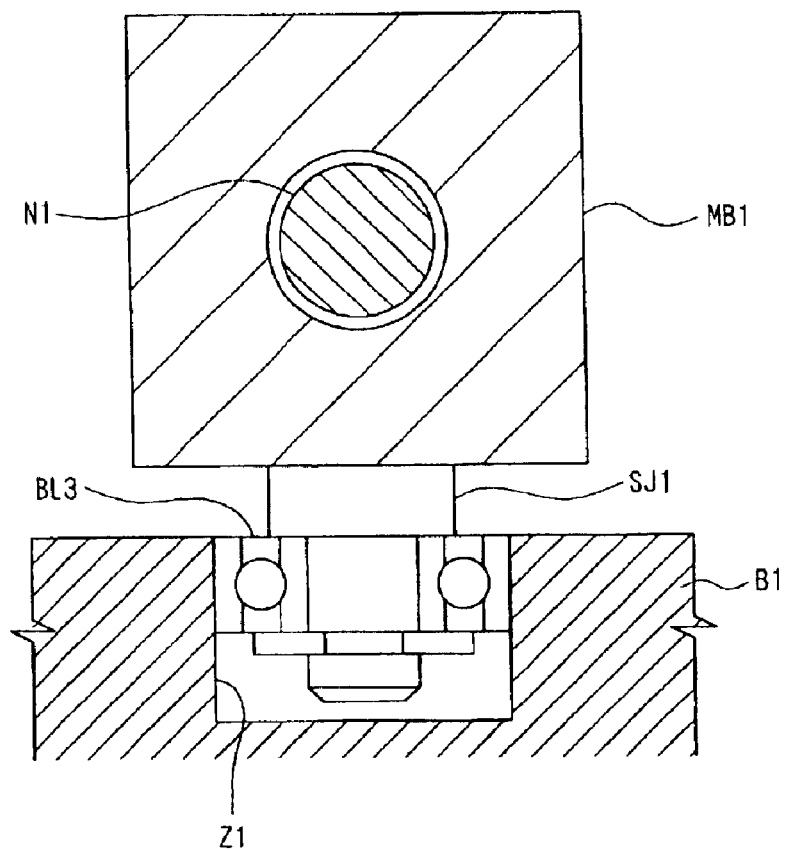
FIG. 3 is a cross-sectional view of a rotation prevention mechanism for moving blocks in the robot hand according to the first embodiment of the present invention.

In FIGS. 1 and 2, 3-degrees-of-freedom universal joints UJ1 and UJ2 are joined to the top right and left parts, respectively, of the wrist portion of the hand H1, and a 2-degrees-of-freedom universal joint UJ3 is joined to the wrist portion of the hand H1 so as to serve as the center of 3-degrees-of-freedom.

The 3-degrees-of-freedom universal joints UJ1 and UJ2 enables the hand H1 to execute up-down swing motions D1 and side-to-side swing motions D2 in response to circular movements about the fulcrum axis of the 2-degrees-of-freedom universal joint UJ3. Further, 2-degrees-of-freedom universal joint UJ3, which serves as the center of the wrist's 3-degrees-of-freedom, is able to make the hand H1 execute twisting motions D3.

On the baseplate B1 are provided projecting portions T1, T1', T2 and T2', to which bearings BL1, BL1', BL2 and BL2' are installed respectively.

Between the projecting portions T1 and T1' a screw N1 is installed such that it is supported by the bearings BL1 and BL1', while a screw member N2 is installed between the projecting portions T2 and T2' such that it is supported by the bearings BL2 and BL2'.

A moving block MB1 is provided between the projecting portions T1 and T1', and a moving block MB2 is provided between the projecting portions T2 and T2'. Screw grooves corresponding to the threads of screws N1 and N2 are formed in moving blocks MB1 and MB2, and the moving blocks MB1 and MB2 are connected to screws N1 and N2 respectively such that their screw grooves in the blocks mate with the screws' respective threads.

Further, each of the moving blocks MB1 and MB2 is provided with a rotation prevention pin, and the base plate B1 has guide grooves Z1 and Z2 formed along the direction of movement of moving blocks MB1 and MB2 respectively, with the rotation prevention pins being inserted into the respective guide grooves Z1 and Z2.

FIG. 3 is a cross-sectional view of a rotation prevention mechanism for the moving blocks in the robot hand according to the first embodiment of the present invention.

At the bottom of the moving block MB1 in FIG. 3, for example, there is provided a rotation prevention pin SJ1 which is in contact with the guide groove Z1 via a bearing BL3.

2-degrees-of-freedom universal joints UJ1' and UJ2' are installed to the moving blocks MB1 and MB2, respectively, and these 2-degrees-of-freedom universal joints UJ1' and UJ2' are coupled to 3-degrees-of-freedom universal joints UJ1 and UJ2, respectively, via connecting rods RD1 and RD2.

On the base plate B1, motors M1 and M2 are respectively installed to the rear of the projecting portions T1 and T2, which are coupled to the screws N1 and N2, respectively, via couplings CP1 and CP2.

Further, towards the forward end of the base plate B1 is installed a motor M3, whose shaft JM is coupled to the 2-degrees-of-freedom universal joint UJ3 via a reduction gear G1.

Next is described the operation of the robot hand in FIGS. 1 and 2.

In order to make the hand H1 execute up-down swing motion D1, motors M1 and M2 are run in the same rotational direction, thus causing screws N1 and N2 to rotate in the same direction.

When this happens, each of the moving blocks MB1 and MB2 moves linearly in the same direction along the corresponding screws N1 and N2, and linear motion components of the moving blocks MB1 and MB2 that move in the same direction are transmitted to the 3-degrees-of-freedom universal joints UJ1 and UJ2 respectively via the connecting rods RD1 and RD2.

Since the 3-degrees-of-freedom universal joints UJ1 and UJ2 are joined to the top right and left parts, respectively, of the wrist portion of the hand H1 while the 2-degrees-of-freedom universal joints UJ3 is installed to the wrist portion of the hand H1 so as to serve as the center for the 3-degrees-of-freedom, the joints UJ1 and UJ2 enable the hand H1 to execute up-down swing motions (D1) by rotating about the horizontal axis JS of the joint UJ3.

In order to make the hand H1 execute side-to-side swing motions D2, the motors M1 and M2 are run in opposite rotational directions, thus causing the screws N1 and N2 to rotate in opposite directions.

When this happens, each of the moving blocks MB1 and MB2 moves linearly in opposite directions along the corresponding screws N1 and N2, and linear motion components of the moving blocks MB1 and MB2 that move in opposite directions are transmitted to the 3-degree-of-freedom universal joints UJ1 and UJ2 respectively via connecting rods RD1 and RD2.

Since the 3-degrees-of-freedom universal joints UJ1 and UJ2 are joined to the top right and left parts, respectively, of the wrist portion of the hand H1 while the 2-degrees-of-freedom universal joint UJ3 is joined to the wrist portion of the hand H1 so as to serve as the center for the 3-degrees-of-freedom, the joints UJ1 and UJ2 enables the hand H1 to execute side-to-side swing motions (D2) by rotating about the vertical axis JH of the joint UJ3.

In order to convert a rotational motion of the screws N1 and N2 into a linear motion of the moving blocks MB1 and MB2, the latter must be prevented from rotating together with the screws. This can be accomplished by providing the blocks with rotation prevention pins. For example, the moving block MB1 includes a rotation prevention pin SJ1 which directs it along the guide groove Z1, thus preventing the blocks MB1 and MB2 from rotating.

In order to make the hand H1 execute twisting rotation D3, the motor M3 is run, thus causing the 2-degrese-of-freedom universal joint UJ3 to rotate about the shaft JM of the motor M3.

When this happens, the hand H1 rotates about the shaft (rotational axis) JM, as the 2-degrees-of-freedom universal joint UJ3 rotates. In this way, a twisting rotation D3 of the hand H1 is executed.

The top right and left end of the hand H1 are joined to the moving blocks MB1 and MB2 via the 3-degrees-of-freedom universal joints UJ1 and UJ2 and 2-degrees-of-freedom universal joints UJ1' and UJ2'. Thus, even when the 3-degrees-of-freedom universal joints UJ1 and UJ2 move on the circumference around the rotation axis JM as the hand H1 makes a twisting rotation D3, it is possible to permit the 3-degrees-of-freedom universal joints UJ1 and UJ2 to follow the hand's twisting rotation by having the connecting rods RD1 and RD2 cross each other.

Thus the provision of the 3-degree-of-freedom universal joints UJ1 and UJ2 and the 2-degree-of-freedom universal joint UJ3 at the wrist portion makes it possible to have the rotation centers of the 3-degrees-of-freedom coincide at a single point, while keeping the three rotational axes JH, JS and JM orthogonal to each other.

This means that wrist movements of 3 degrees of freedom (up-down swing motion D1, side-to-side swing motion D2 and twisting rotation D3) can be executed merely by implementing simple drive control of the motors M1–M3, with the result that the computational processing for operation can be simplified, and agile and precise positioning control can be implemented.

Furthermore, the 3-degrees-of-freedom universal joints UJ1 and UJ2 and the 2-degrees-of-freedom universal joints UJ1', UJ2' and UJ3 are provided with stepped bearing screws which are screwed into their cruciform members via bearings, thereby simplifying their structure.

Figure 4:
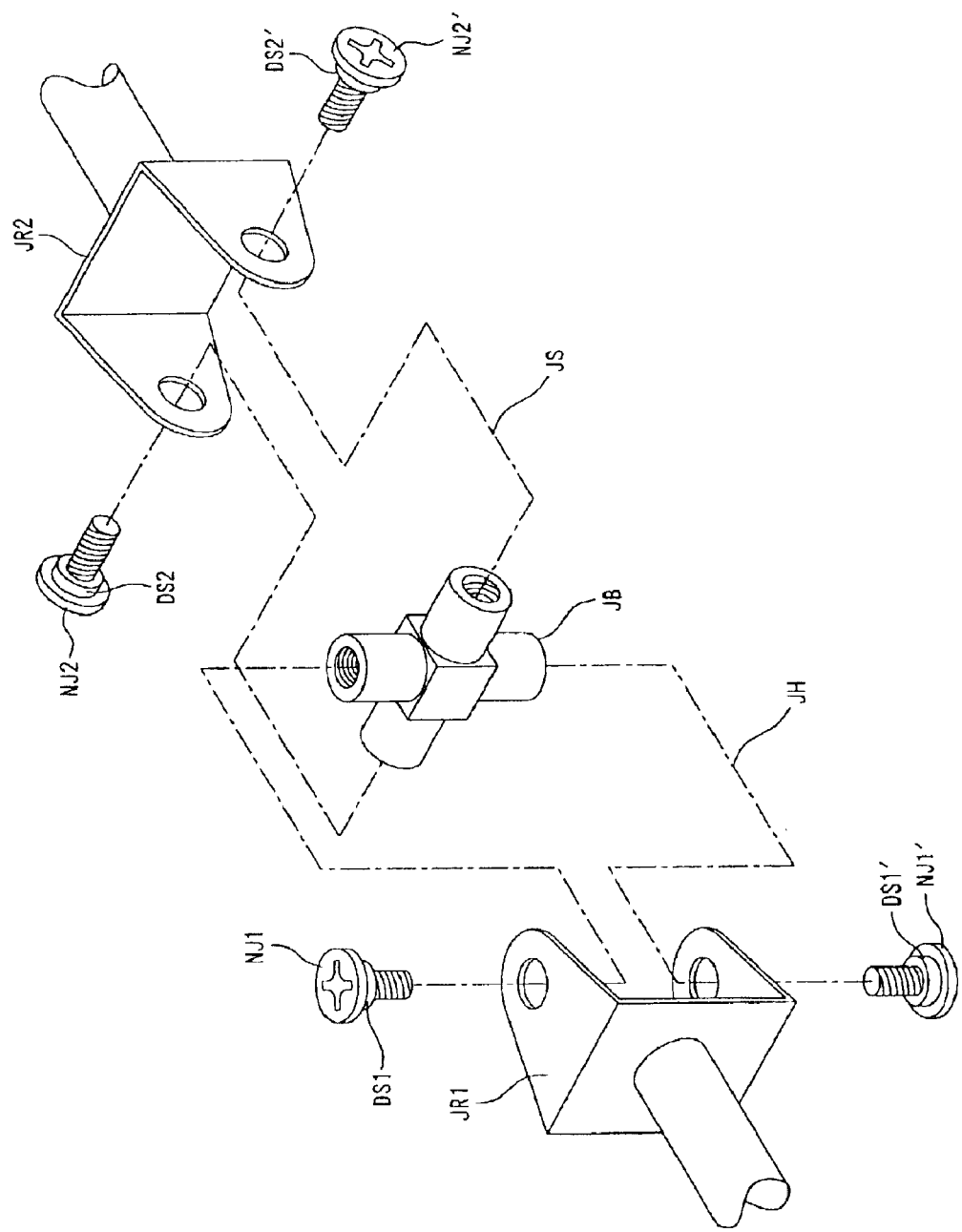
FIG. 4 is an exploded perspective view showing the structure of universal joints in the robot hand according to the first embodiment of the present invention.

FIG. 4 is an exploded perspective view showing the structure of the universal joints in the robot hand according to the first embodiment of the present invention.

In FIG. 4, stepped bearing screws NJ1, NJ1', NJ2 and NJ2' are provided respectively with steps DS1, DS2, DS1' and DS2' for receiving yokes JR1 and JR2.

The stepped bearing screws NJ1, NJ1', NJ2 and NJ2' are screwed through the yokes JR1 and JR2 into the cruciform member JB.

Because of this arrangement, the yokes JR1 and JR2 are able to rotate about the horizontal axis JS and the vertical axis JH simply by means of the stepped bearing screws NJ1, NJ1', NJ2 and NJ2' screwed into the cruciform member JB, thus making it possible to simplify the structure of the 3-degrees-of-freedom universal joints UJ1 and UJ2 and of the 2-degrees-of-freedom universal joints UJ1', UJ2' and UJ3.

FIG. 5(a) is a diagram showing coordinates of the various points, for the purpose of explicating the drive method for a robot hand according to an embodiment of the present invention. FIG. 5(b) is a diagram showing the coordinates after a rotation about the x-axis has been made.

Figure 5:
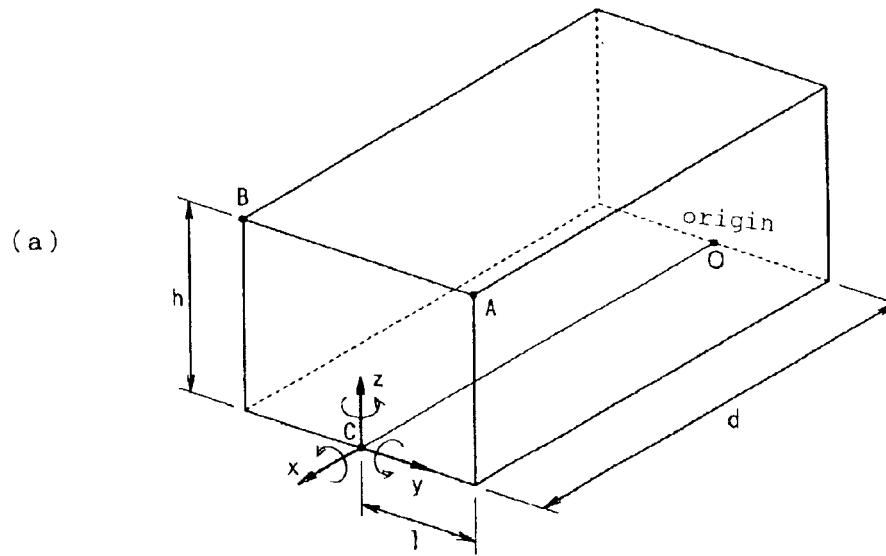
FIG. 5(a) is a diagram showing coordinates of the various points, for the purpose of explicating the drive method for a robot hand according to an embodiment of the present invention.
FIG. 5(b) is a diagram showing the coordinates after a rotation about the x-axis has been made.
Figure 5:
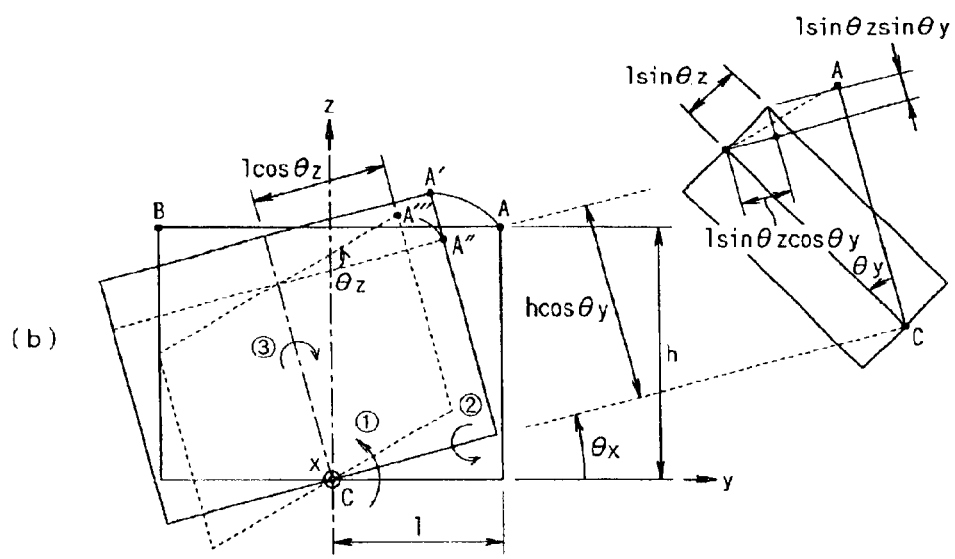

In FIG. 5, O is the origin (0, 0, 0), C is the rotation center of the 2-degrees-of-freedom universal joint UJ3 of FIG. 1, A is the center of 3-degrees-of-freedom universal joint UJ1, B is the center of 3-degrees-of-freedom universal joint UJ2, $\theta_X$ is the angle of rotation about the x-axis, $\theta_Y$ is the angle of rotation about the y-axis, $\theta_Z$ is the angle of rotation about the z-axis, d is the distance between O and C, h is the distance along the z-axis between the rotation center of the 2-degrees-of-freedom universal joint UJ3 and the centerline of the 3-degrees-of-freedom universal joints UJ1 and UJ2, l is the distance along the y-axis between the rotation center of the 2-degrees-of-freedom universal joint UJ3 and the centerline of the 3-degrees-of-freedom universal joints UJ1 and UJ2, A' is the point to which point A is rotated (①) by $\theta_X$, A" is the point to which point A' is rotated (②) by $\theta_Y$, and A'" is the point to which point A" is rotated (③) by $\theta_Z$.

The coordinates of point C (Xc, Yc, Zc) are equal to (d, 0, 0), while those of point $A_3$ ($X_{A3}$, $Y_{A3}$, $Z_{A3}$) are given by:

$$X_{A3} = d + h \times \sin \theta_Y - l \times \sin \theta_Z \times \cos \theta_Y \quad (1)$$

$$Y_{A3} = l \times \cos \theta_X \times \cos \theta_Z - (h \times \cos \theta_Y + l \times \sin \theta_{Z \times \sin \theta_Y}) \times \sin \theta_X \quad (2)$$

$$Z_{A3} = l \times \cos \theta_Z \times \sin \theta_X + (h \times \cos \theta_Y + l \times \sin \theta_Z \times \sin \theta_Y) \times \cos \theta_X \quad (3)$$

The coordinates of point B3 ($X_{B3}$, $Y_{B3}$, $Z_{B3}$) are given by:

$$X_{B3} = d + h \times \sin \theta_Y + l \times \sin \theta_Z \times \cos \theta_Y \quad (4)$$

$$Y_{B3} = -l \times \cos \theta_X \times \cos \theta_Z - (h \times \cos \theta_Y - l \times \sin \theta_X \times \sin \theta_Y) \times \sin \theta_X \quad (5)$$

$$Z_{B3} = -l \times \cos \theta_Z \times \sin \theta_X + (h \times \cos \theta_Y - l \times \sin \theta_Z \times \sin \theta_Y) \times \cos \theta_X \quad (6)$$

In cases where a twisting rotation of the wrist is shifted to the elbow portion, giving just 2-degrees-of-freedom to the wrist, $\theta_X$ can be taken as equal to 0. As a result, the coordinates of point $A_3$ ($X_{A3}$, $Y_{A3}$, $Z_{A3}$) will be given by:

$$X_{A3}=d+h\times\sin\theta_Y-1\times\sin\theta_Z\times\cos\theta_Y \quad (1)$$

$$Y_{A3}=1\times\cos\theta_Z \quad (2)$$

$$Z_{A3}=h\times\cos\theta_Y+1\times\sin\theta_Z\times\sin\theta_Y \quad (3)$$

And the coordinates of point $B_3$ ($X_{B3}$, $Y_{B3}$, $Z_{B3}$) in this case will be given by:

$$X_{B3}=d+h\times\sin\theta_Y+1\times\sin\theta_Z\times\cos\theta_Y \quad (4)$$

$$Y_{B3}=-1\times\cos\theta_Z \quad (5)$$

$$Z_{B3}=h\times\cos\theta_Y-1\times\sin\theta_Z\times\sin\theta_Y+tm \quad (6)$$

As a result, calculation can be simplified by shifting twisting rotation of the wrist to the elbow portion.

Figure 6:
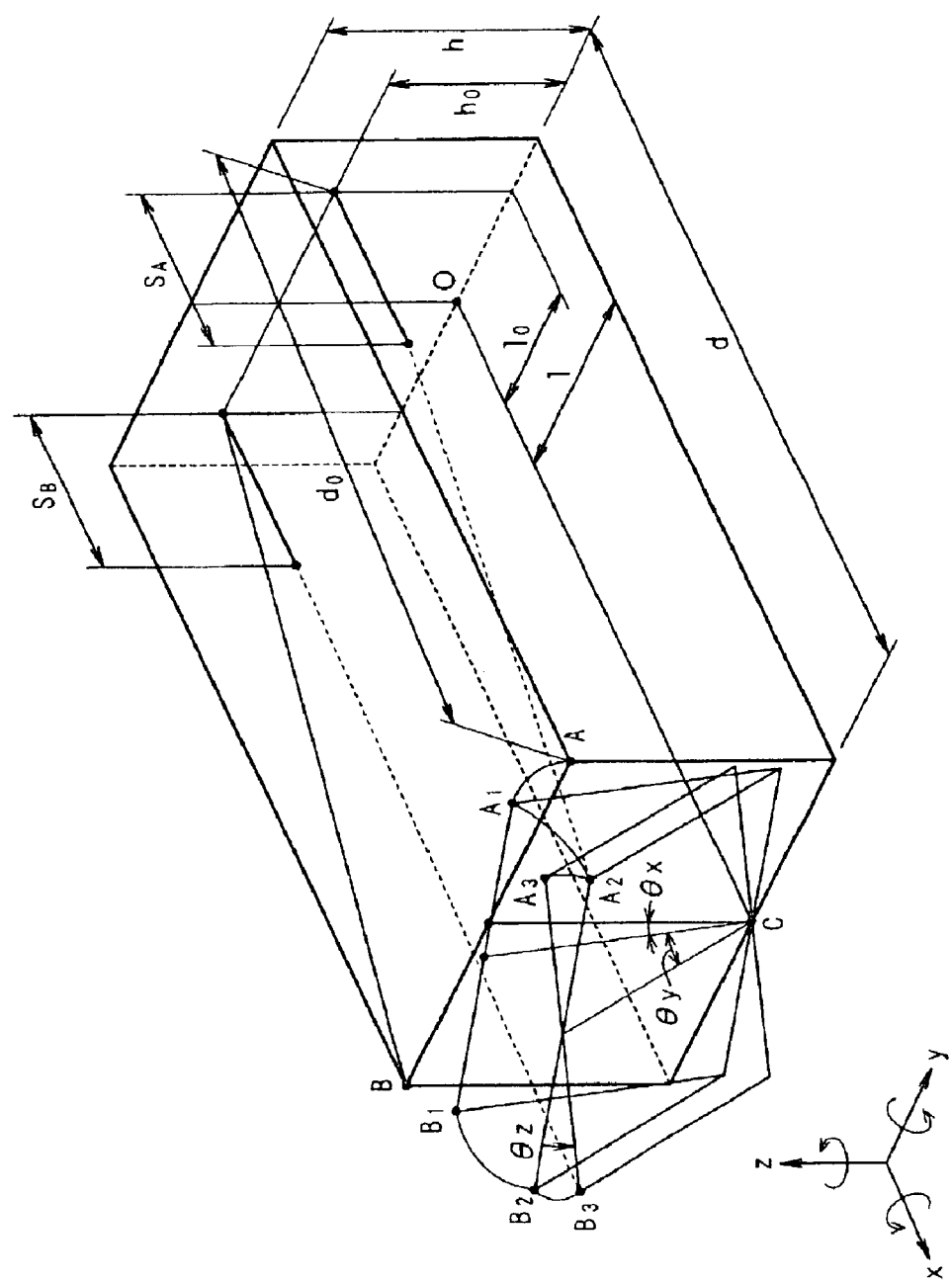
FIG. 6 is a diagram showing coordinates of the various points after a rotation has been made, for the purpose of explicating the drive method for a robot hand according to an embodiment of the present invention.

FIG. 6 is a diagram showing coordinates of the various points when shifted by rotations, for the purpose of explaining the drive method for a robot hand according to an embodiment of the present invention.

In FIG. 6, O is the origin (0, 0, 0), C is the rotation center of the 2-degrees-of-freedom universal joint UJ3 of FIG. 1, A is the center of 3-degrees-of-freedom universal joint UJ1, B is the center of 3-degrees-of-freedom universal joint UJ2, $\theta_X$ is the angle of rotation about the x-axis, $\theta_Y$ is the angle of rotation about the y-axis, $\theta_Z$ is the angle of rotation about the z-axis, d is the distance between O and C, h is the distance along the z-axis between the rotation center of the 2-degrees-of-freedom universal joint UJ3 and the centerline of the 3-degrees-of-freedom universal joints UJ1 and UJ2, l is the distance along the y-axis between the rotation center of the 2-degrees-of-freedom universal joint UJ3 and the centerline of the 3-degrees-of-freedom universal joints UJ1 and UJ2, do is the length of the connecting rods RD1 and RD2, ho is the distance along the z-axis between the origin O and the moving blocks MB1 and MB2, $l_0$ is the distance along the y-axis between the origin O and the moving blocks MB1 and MB2, $A_1$ is the point to which point A is rotated about the x-axis by $\theta_X$, $A_2$ is the point to which point $A_1$ is rotated about the y-axis by $\theta_Y$, $A_3$ is the point to which point $A_2$ is rotated about the x-axis by $\theta_Z$, $B_1$ is the point to which point B is rotated about the x-axis by $\theta_X$, $B_2$ is the point to which point $B_1$ is rotated about the y-axis by $\theta_Y$, $B_3$ is the point to which point $B_2$ is rotated about the x-axis by $\theta_Z$, and $S_A$ and $S_B$ are the distances moved by the moving blocks MB1 and MB2 respectively.

The following equation is given:

$$d_0=\sqrt{(d^2+(l-l_0)^2+(h-h_0)^2)} \quad (7)$$

Hence, $$d_0^2=d^2+(l-l_0)^2+(h-h_0)^2 \quad (8)$$

The following equation is also given:

$$(X_{A3}-S_A)^2+(Y_{A3}-l_0)^2+(Z_{A3}-h_0)^2=d_0^2 \quad (9)$$

Hence, $$S_A=X_{A3}-\sqrt{(d_0^2-(Y_{A3}-l_0)^2-(Z_{A3}-h_0)^2)} \quad (10)$$

Similarly, $$(X_{B3}-S_B)^2+(Y_{B3}-l_0)^2+(Z_{B3}-h_0)^2=d_0^2 \quad (11)$$

Hence, $$S_B=X_{B3}-\sqrt{(d_0^2-(Y_{B3}-l_0)^2-(Z_{B3}-h_0)^2)} \quad (12)$$

Consequently, when the angles of rotation $\theta_X$, $\theta_Y$, and $\theta_Z$ of the hand H1 about the x-, y- and z-axes respectively are given, the distance moved by the moving blocks MB1 and MB2 can be worked out by calculating the coordinates of point $A_3$ ($X_{A3}$, $Y_{A3}$, $Z_{A3}$) and of point $B_3$ ($X_{B3}$, $Y_{B3}$, $Z_{B3}$) according to equations (1) through (6) and substituting the resulting values in equations (10) and (11).

This means that drive control of each motor M1 and M2 can be implemented on the basis of kinematical coordinate calculations, thus permitting agile and precise positioning control.

Figure 7:
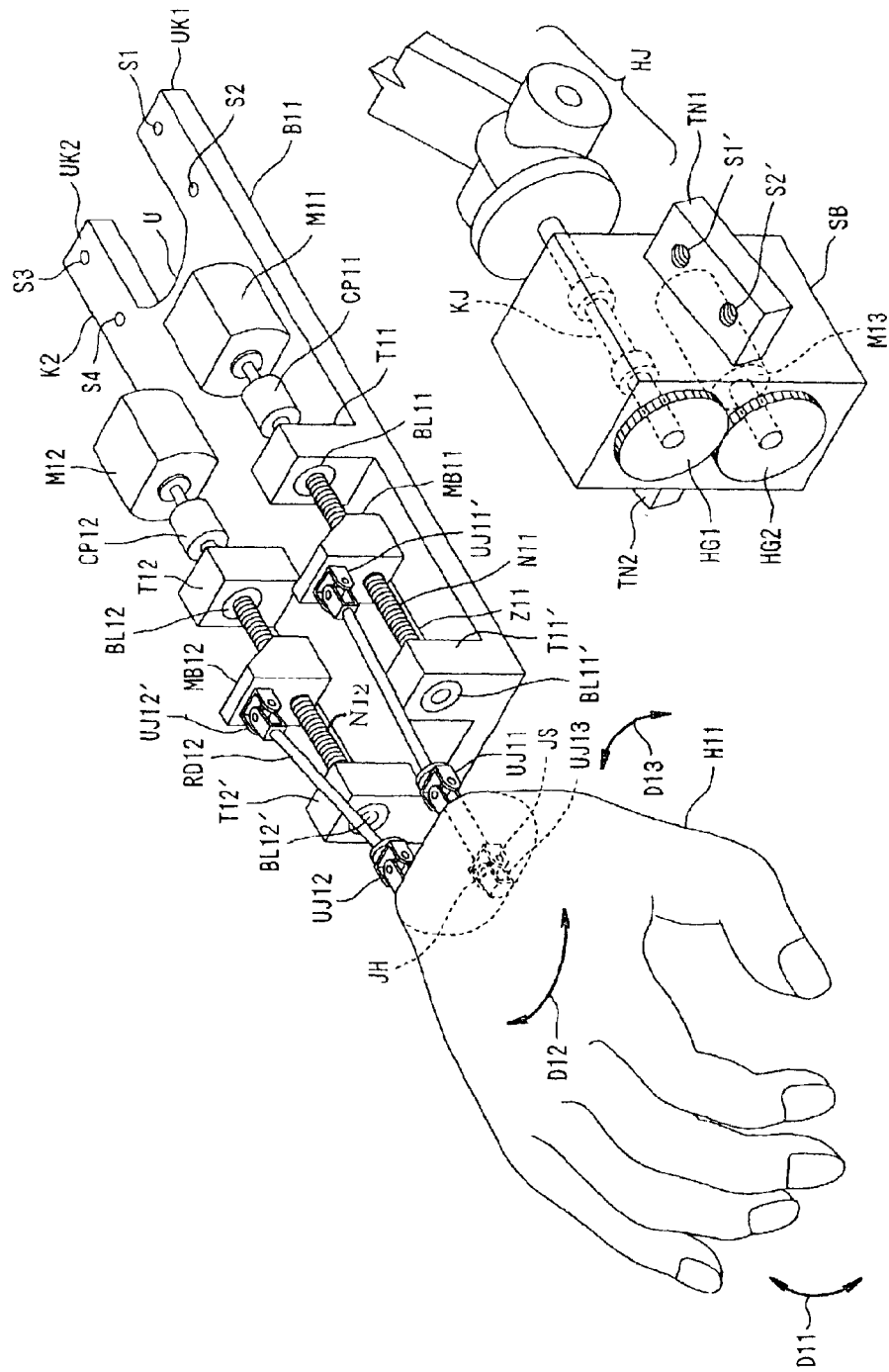
FIG. 7 is a perspective view showing a general configuration of a robot hand according to a second embodiment of the present invention.
Figure 8:
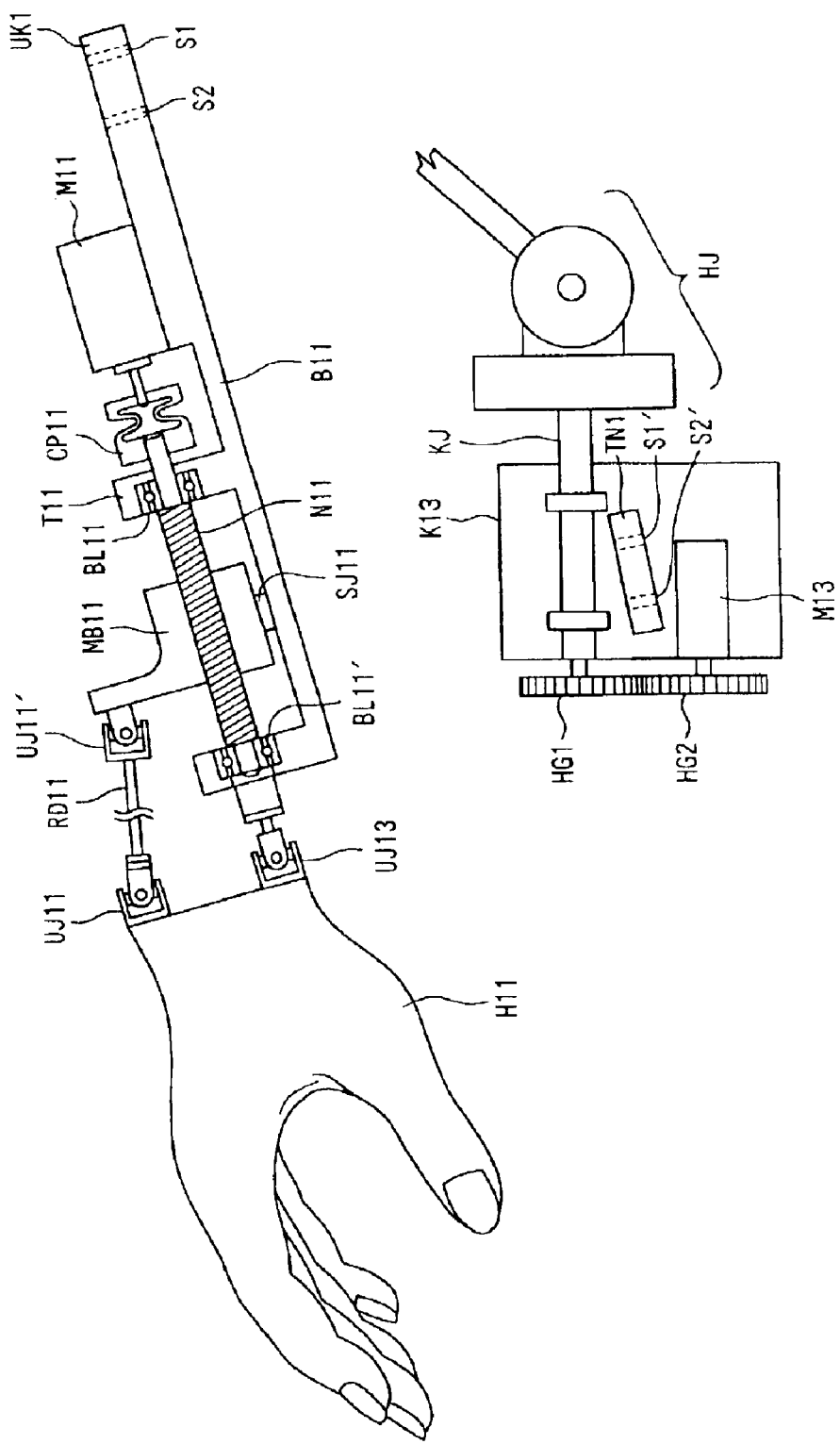
FIG. 8 is a side view showing a general configuration of a robot hand according to the second embodiment of the present invention.

FIG. 7 is a perspective view, showing the summarized configuration of a robot hand according to a second embodiment of the present invention. FIG. 8 is a side view, showing the summarized configuration of the robot hand according to the second embodiment of the present invention. In the second embodiment, the twisting rotation of the wrist is shifted to the elbow portion, giving just 2-degrees-of-freedom to the wrist, so that 2-degrees-of-freedom are sufficient for universal joints UJ11 and UJ12 located at the top right and left parts of the wrist portion.

In FIGS. 7 and 8, 2-degrees-of-freedom universal joints UJ11 and UJ12 are joined to the top right and left parts, respectively, of the wrist portion of the hand H1, and a 2-degrees-of-freedom universal joint UJ13 is joined to the wrist portion of the hand H1 so as to serve as the center of 2-degrees-of-freedom.

The 2-degrees-of-freedom universal joints UJ11 and UJ12 enables the hand H1 to execute up-down swing motion D11 and side-to-side swing motion D12 in response to circular movements about the fulcrum axis of 2-degree-of-freedom universal joint UJ13.

On a base plate B11 are provided projecting portions T11, T11', T12 and T12', to which bearings BL11, BL11', BL12 and BL12' are installed respectively.

Between the projecting portions T11 and T11' a screw N11 is installed such that it is supported by the bearings BL11 and BL11', while a screw N12 is installed between projecting portions T12 and T12' such that it is supported by the bearings BL12 and BL12'.

A moving block MB11 is provided between the projecting portions T11 and T11', and a moving block MB12 is provided between the projecting portions T12 and T12'. Screw grooves corresponding to the threads of screws N11 and N12 are formed in moving blocks MB11 and MB12, and the moving blocks MB11 and MB12 are transpierced by screws N11 and N12 respectively such that their screw grooves mate with the screws' respective threads.

Further, each of moving blocks MB11 and MB12 is provided with a rotation prevention pin, the base plate B11 has guide grooves Z11 and Z12 formed along the direction of movement of the moving boards MB11 and MB12 respectively, and the rotation prevention pins are inserted into the respective guide grooves Z11 and Z12.

2-degrees-of-freedom universal joints UJ11' and UJ12' are installed to moving blocks MB11 and MB12 respectively, and these 2-degrees-of-freedom universal joints UJ11' and UJ12' are connected to 2-degrees-of-freedom universal joints UJ11 and UJ12 respectively via connecting rods RD11 and RD12.

On the baseplate B11, motors M11 and M12 are installed respectively to the rear of the projecting portions T11 and T12, and the motors are coupled to the screws N11 and N12 respectively via couplings CP11 and CP12.

Further, at the rear end of the baseplate B11, a recessed portion U is formed for fitting a support block SB thereinto, and in extended portions UK1 and UK2 on either side of the recessed portion U there are provided screw holes S1–S4.

The support block SB is for securing the baseplate B11 and is connected to the elbow portion HJ via a fixed shaft KJ which serves as the rotation center of the support block SB.

Ledges TN1 and TN2 for mounting the extended portions UK1 and UK2 of the base plate B11 are provided on either side of the support block SB, and screw holes S1' and S2' are provided in the ledges TN1 and TN2.

When the extended portions UK1 and UK2 of the base plate B11 are mounted onto the ledges TN1 and TN2, the base plate B11 can be secured to the support block SB by, for example, driving screws into the holes formed by S1 and S1' and by S2 and S2'.

Further, the support block SB includes a motor M13 whose shaft is coupled to a gearwheel HG2, and a gearwheel HG1 is installed to the fixed shaft KJ (which is connected to the elbow portion HJ) such that it meshes with the gearwheel HG2.

Next is described the operation of the robot hand in FIGS. 7 and 8.

In order to make the hand H11 execute up-down swing motions D11, motors M11 and M12 are run in the same rotational direction, thus causing screws N11 and N12 to rotate in the same direction.

When this happens, moving blocks MB11 and MB12 move linearly in the same direction along the screws N11 and N12, and linear motion components of the moving blocks MB11 and MB12 that moves in the same direction are transmitted to the 2-degrees-of-freedom universal joints UJ11 and UJ12 respectively via connecting rods RD11 and RD12.

Since the 2-degrees-of-freedom universal joints UJ11 and UJ12 are joined to the top right and left parts, respectively, of the wrist portion of the hand H11 while the 2-degrees-of-freedom universal joint UJ13 is joined to the wrist portion of the hand H11 so as to serve as the center for the 2-degrees-of-freedom, the joints UJ11 and UJ12 enables the hand H11 to execute up-down swing motion (D11) by rotating about the horizontal axis JS of the joint UJ13.

In order to make the hand H11 execute side-to-side swing motions D12, the motors M11 and M12 are run in opposite rotational directions, thus causing the screws N11 and N12 to rotate in opposite directions.

When this happens, each moving block MB11 and MB12 moves linearly in opposite directions along the corresponding screws N11 and N12, and linear motion components of moving blocks MB11 and MB12 that moves in opposite direction are transmitted to the 2-degrees-of-freedom universal joints UJ11 and UJ12 respectively via the connecting rods RD11 and RD12.

Since the 2-degrees-of-freedom universal joints UJ11 and UJ12 are joined to the top right and left parts, respectively, of the wrist portion of the hand H11 while the 2-degrees-of-freedom universal joint UJ13 is joined to the wrist portion of the hand H11 so as to serve as the center for the 2-degrees-of-freedom, joints UJ11 and UJ12 enables the hand H11 to execute up-down swing motion (D12) by rotating about the vertical axis JH of joint UJ13.

In order to convert rotational motions of the screws N11 and N12 into linear motions of the moving blocks MB11 and MB12, the latter must be prevented from rotating together with the screws. This can be accomplished by providing the blocks with rotation prevention pins. For example, the moving block MB11 is provided with a rotation prevention pin SJ11 which directs it along the guide groove Z11, thus preventing the blocks MB11 and MB12 from rotating.

And in order to execute rotations D13 of the hand H11, the motor M13 is run, so as to rotate the gearwheel HG2.

Thereupon the rotational force of the gearwheel HG2 is transmitted to the gearwheel HG1. However, the gearwheel HG1 is fastened to the fixed shaft KJ, so the gearwheel HG2 is subjected to reaction from the gearwheel HG1. This causes the gearwheel HG2 to rotate around the circumference of the gearwheel HG1, thereby effecting twisting rotation of the entire arm up to the elbow portion HJ.

That is, the fixed shaft KJ is fastened to the elbow portion HJ, the support block SB is able to rotate about the fixed shaft KJ, and the motor M13 is fastened to the support block SB.

As a result, when the gearwheel HG2 turns, it rotates along the circumference of the gearwheel HG1 because the latter is fastened to the fixed shaft KJ, whereby the support block SB and the motor M13 rotate as an integrated whole around the circumference of the fixed shaft KJ.

Therefore the base plate B11, which is fastened to the support block SB, rotates on the circumference around the fixed shaft KJ as the support block SB rotates, causing the hand H11 to rotate about the fixed shaft KJ.

The base plate B11 should preferably be fastened to the support block SB such that the third universal joint UJ13 is located on the line of the axis of the fixed shaft KJ. This will permit rotation in any desired direction around the x-, y- and z-axes even when the mechanism for wrist rotation is shifted to the elbow portion.

The third universal joint UJ13 may be made to lie on the line of the axis of the fixed shaft KJ when the baseplate B11 is fastened to the support block SB by, for example, installing the ledges TN1 and TN2 to the support block at an inclined angle.

This makes it possible to secure the baseplate B11 to the support block SB simply by mounting the extended portions UK1 and UK2 of the base plate B11 onto the ledges TN1 and TN2 so that the third universal joints UJ13 will be positioned onto the axis of line of the fixed shaft KJ.

Thus, according to the second embodiment described above, the mechanism for wrist rotation is shifted to the elbow portion, giving just 2-degrees-of-freedom to the wrist and thereby permitting the manipulation unit to be even more compact and to have a simpler control.

In the foregoing descriptions of embodiments it is assumed that the method for making the universal joints UJ1 and UJ2 (or UJ11 and UJ12) execute circular rotation motions about universal joint UJ3 (or UJ13) uses the motors M1 and M2 (or M11 and M12) and the screws N1 and N2 (or N11 and N12), but another rotational-to-linear motion conversion mechanism such as rack-and-pinion could alternatively be used instead of the screws.

Further, linear motors could alternatively be used to drive the universal joints UJ1 and UJ2 (or UJ11 and UJ12).

Additionally, where operational positions are measured to apply control, potentiometers, encoders, linear sensors or the like may be used to measure amounts of rotational and/or linear motions of the actuators, and potentiometers or encoders may be used to measure rotation angles of the universal joints.

Further, although the foregoing descriptions of the embodiments are given taking an application of the invention to a robot arm as an example, it may also be applied to the elbow, shoulder, neck or other joints of a robot, to mechanisms for motion of a robot's eye, to the joints of a manipulator, or to the platforms for an omnidirectional projector and a tracking camera, and so on.

As the foregoing has described, according to the present invention, the rotation centers of the 3-degrees-of-freedom can be made to coincide at a single point while keeping the rotational axes orthogonal to each other, thereby making it possible to perform movement operations easily and to make a manipulation unit more lightweight and more compact. These advantages yield the further advantage of agile and precise control of positioning.

The entire disclosure of Japanese Application No. 2001-367328 filed Nov. 30, 2001 is incorporated by reference herein.

What is claimed is:

1. A manipulation unit comprising:

first and second universal joints that allow up-down and side-to-side swing motions to be made in response to linear motions, a third universal joint that serves as the center of 2-degrees-of-freedom and enables twisting rotations, a rotation means that rotates the first and second universal joints around a fixed shaft, a first linear actuator which moves the first universal joint in linear motion, a second linear actuator which moves the second universal joint in linear motion, fastening blocks which hold the first, second and third universal joints and the first and second linear actuators securely, a support block which supports the fastening blocks, bearing units which support the supports block such that it is able to rotate around said fixed shaft, a rotation motor which is installed in the support block, and gearwheels which transmit a rotational force of the rotation motor to the fixed shaft, wherein the fastening blocks are fastened to the support block such that the third universal joint is located on a line of the fixed shaft's axis.

* * * * *